United States Patent
Zhu et al.

(10) Patent No.: US 7,560,451 B2
(45) Date of Patent: Jul. 14, 2009

(54) ASPARTYL PROTEASE INHIBITORS

(75) Inventors: Zhaoning Zhu, Plainsboro, NJ (US); Andrew W. Stamford, Chatham Township, NJ (US); Brian McKittrick, New Vernon, NJ (US)

(73) Assignee: Schering Corporation, Kenilworth, NJ (US)

( * ) Notice: Subject to any disclaimer, the term of this patent is extended or adjusted under 35 U.S.C. 154(b) by 281 days.

(21) Appl. No.: 11/589,387

(22) Filed: Oct. 30, 2006

(65) Prior Publication Data

US 2007/0099875 A1 May 3, 2007

Related U.S. Application Data

(60) Provisional application No. 60/731,702, filed on Oct. 31, 2005.

(51) Int. Cl.
C07D 411/04 (2006.01)
A61K 31/553 (2006.01)

(52) U.S. Cl. .................. 514/211.1; 540/489
(58) Field of Classification Search ............ 540/489; 514/211.1
See application file for complete search history.

(56) References Cited

FOREIGN PATENT DOCUMENTS

| WO | WO 03/059346 | 7/2003 |
|---|---|---|
| WO | WO 2005/058311 | 6/2005 |
| WO | WO 2006/138217 | 12/2006 |

OTHER PUBLICATIONS

Applicants' Copending U.S. Appl. No. 10/910,987, filed Aug. 4, 2004. Applicants' Ref: CN06095.
Applicants' Copending U.S. Appl. No. 10/911,030, filed Aug. 4, 2004. Applicants' Ref: CN06096.
Applicants' Copending U.S. Appl. No. 11/010,772, filed Dec. 13, 2004. Applicants' Ref: CN06136.
Applicants' Copending U.S. Appl. No. 12/331,787, filed Dec. 10, 2008, (DIV of U.S. Appl. No. 11/010,772). Applicants' Ref: CN06136US04.
Applicants' Copending U.S. Appl. No. 11/149,027, filed Jun. 9, 2005. Allowed. Applicants' Ref: CN06136-01.
Applicants' Copending U.S. Appl. No. 11/710,582, filed Feb. 23, 2007. Applicants' Ref: CN06136-02US04.
Applicants' Copending U.S. Appl. No. 11/185,419, filed Jul. 20, 2005. Applicants' Ref: CN06209.
Applicants' Copending U.S. Appl. No. 11/189,346, filed Jul. 26, 2005. Applicants' Ref: CN06210.
Applicants' Copending U.S. Appl. No. 11/451,262, filed Jun. 12, 2006. Applicants' Ref: CN06358.
Applicants' Copending U.S. Appl. No. 11/451,065, filed Jun. 12, 2006. Applicants' Ref: CN06359.
Applicants' Copending U.S. Appl. No. 11/451,194, filed Jun. 12, 2006. Applicants' Ref: CN06360.
Applicants' Copending U.S. Appl. No. 11/451,064, filed Jun. 12, 2006. Applicants' Ref: CN06361.
Applicants' Copending U.S. Appl. No. 11/451,541, filed Jun. 12, 2006. Applicants' Ref: CN06363.
Applicants' Copending U.S. Appl. No. 11/451,074, filed Jun. 12, 2006. Applicants' Ref: CN06371.
Applicants' Copending U.S. Appl. No. 11/451,195, filed Jun. 12, 2006. Applicants' Ref: CN06372.
Applicants' Copending U.S. Appl. No. 11/586,151, filed Oct. 25, 2006. Applicants' Ref: CN06403.
Applicants' Copending U.S. Appl. No. 11/589,387, filed Oct. 30, 2006. Applicants' Ref: CN06404.
Applicants' Copending U.S. Appl. No. 11/759,336, filed Jun. 7, 2007. Applicants' Ref: CN06485.
International Search Report for PCT/US 2006/042193, mailed Apr. 2, 2007 (3 pages) for CN06404.
PCT Written Opinion of the International Searching Authority for PCT/US 2006/042193, (8 pages) for CN06404.

*Primary Examiner*—Bruck Kifle
(74) *Attorney, Agent, or Firm*—Keith D. MacMillan; William Y. Lee

(57) ABSTRACT

Disclosed are compounds of the formula I

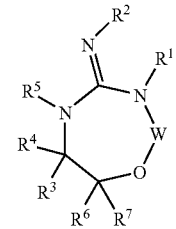

or a stereoisomer, tautomer, or pharmaceutically acceptable salt or solvate thereof, wherein W, $R^1$, $R^2$, $R^3$, $R^4$, $R^5$, $R^6$, and $R^7$ are as defined in the specification; and pharmaceutical compositions comprising the compounds of formula I.

Also disclosed is the method of inhibiting aspartyl protease, and in particular, the methods of treating cardiovascular diseases, cognitive and neurodegenerative diseases, and the methods of inhibiting of Human Immunodeficiency Virus, plasmepins, cathepsin D and protozoal enzymes.

Also disclosed are methods of treating cognitive or neurodegenerative diseases using the compounds of formula I in combination with a cholinesterase inhibitor or a muscarinic antagonist.

20 Claims, No Drawings

ASPARTYL PROTEASE INHIBITORS

This Application claims the benefit of U.S. Provisional Application No. 60/731,702 filed Oct. 31, 2005.

FIELD OF THE INVENTION

This invention relates to aspartyl protease inhibitors, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

Human aspartic proteases of the A1 (pepsin-like) family are as follows: pepsin A and C, renin, BACE-1, BACE 2, Napsin A, cathepsin D in pathological conditions.

The role of renin-angiotensin system (RAS) in regulation of blood pressure and fluid electrolyte has been well established (Oparil, S, etal. N Engl J Med 1974; 291:381-401/446-57). The octapeptide Angiotensin-II, a potent vasoconstrictor and stimulator for release of adrenal aldosterone, was processed from the precursor decapeptide Angiotensin-I, which in turn is processed from angiotensinogen by the renin enzyme. Angiotensin-II is also found to play roles in vascular smooth muscle cell growth, inflammation, reactive oxygen species generation and thrombosis and influence atherogenesis and vascular damage. Clinically, the benefit of interruption of the generation of angiotensin-II through antagonism of conversion of angiotensin-I has been well known and there are a number of ACE inhibitor drugs on the market. The blockade of the earlier conversion of angiotensinogen to angiotensin-I, i.e. the inhibition of renin enzyme, is expected to have similar but not identical effects. Since renin is an aspartyl protease whose only natural substrate is angiotensinogen, it is believed that there would be less frequent adverse effect for controlling high blood pressure and related symptoms regulated by angiotensin-II through its inhibition.

Another protease, Cathepsin-D, is involved in lysosomal biogenesis and protein targeting, and may also be involved in antigen processing and presentation of peptide fragments. It has been linked to numerous diseases including, Alzheimer's, Disease, connective tissue disease, muscular dystrophy and breast cancer.

Alzheimer's Disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result of β-secretase activity, inhibition of BACE-1 should inhibit formation of Aβ peptides. Thus inhibition of BACE-1 is a therapeutic approach to the treatment of AD and other cognitive and neurodegenerative diseases caused by Aβ deposition.

Human immunodeficiency virus (HIV), is the causative agent of acquired immune deficiency syndrome (AIDS). It has been clinically demonstrated that compounds such as indinavir, ritonavir and saquinavir which are inhibitors of the HIV aspartyl protease result in lowering of viral load. As such, the compounds described herein would be expected to be useful for the treatment of AIDS. Traditionally, a major target for researchers has been HIV-1 protease, an aspartyl protease related to renin.

In addition, Human T-cell leukemia virus type I (HTLV-I) is a human retrovirus that has been clinically associated with adult T-cell leukemia and other chronic diseases. Like other retroviruses, HTLV-I requires an aspartyl protease to process viral precursor proteins, which produce mature virions. This makes the protease an attractive target for inhibitor design. (Moore, et al. Purification of HTLV-I Protease and Synthesis of Inhibitors for the treatment of HTLV-I Infection 55th Southeast Regional Meeting of the American Chemical Society, Atlanta, Ga., US Nov. 16-19, 2003 (2003), 1073. CODEN; 69EUCH Conference, AN 2004:137641 CAPLUS).

Plasmepsins are essential aspartyl protease enzymes of the malarial parasite. Compounds for the inhibition of aspartyl proteases plasmepsins, particularly I, II, IV and HAP, are in development for the treatment of malaria. (Freire, et al. WO 2002074719. Na Byoung-Kuk, et al., Aspartic proteases of Plasmodium vivax are highly conserved in wild isolates, Korean Journal of Parasitology (2004 June), 42(2) 61-6. Journal code: 9435800) Furthermore, compounds used to target aspartyl proteases plasmepsins (e.g. I, II, IV and HAP), have been used to kill malarial parasites, thus treating patients thus afflicted.

Compounds that act as aspartyl protease inhibitors are described, for example, in application U.S. Ser. No. 11/010, 772, filed on Dec. 13, 2004, herein incorporated by reference.

SUMMARY OF THE INVENTION

The present invention relates to compounds having the structural formula I

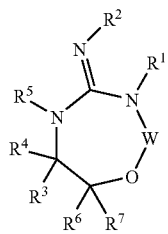

I or an isomer, pharmaceutically acceptable salt, solvate or ester of said compound or said isomer, wherein W is —S(O)—, —S(O)$_2$—, —P(O)(OR$^{15}$)— or —C(=O)—;

$R^1$, $R^2$ and $R^5$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —OR$^{15}$, —CN, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^8$)$_2$;

$R^3$, $R^4$, $R^6$ and $R^7$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —CH$_2$—O—Si(R$^9$)(R$^{10}$)(R$^{19}$), —CN, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$—, —N(R$^{11}$)C(O)N(R$^{12}$)(R$^{13}$), —N(R$^{11}$)C(O)OR$^9$ and —C(=NOH)R$^8$;

or optionally, any two of $R^3$, $R^4$, $R^6$ and $R^7$ together with the carbon atoms to which they are attached form:

a) a 3- to 8-membered cycloalkyl ring optionally substituted by 1 to 5 $R^{23}$ moieties; and b) 1-4 of the atoms in the above 3-8 membered cycloalkyl ring can be replaced by —O—, —S—, —N(R$^{11}$)—, —C(O)—, —S(O)— or —S(O)$_2$—;

$R^8$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

$R^9$ is independently selected from the group consisting of H, alkyl, cycloalkyl, cycloalkylalkyl, heterocycloalkyl, heterocycloalkylalkyl, aryl, arylalkyl, heteroaryl and heteroarylalkyl;

$R^{10}$ is independently selected from the group consisting of H, alkyl, alkenyl, cycloalkyl, cycloalkylalkyl, cycloalkenyl, heterocycloalkyl, heterocycloalkylalkyl, aryl, arylalkyl, heteroaryl, heteroarylalkyl and —N(R$^{15}$)(R$^{16}$);

$R^{11}$, $R^{12}$ and $R^{13}$ are independently selected from the group consisting of H, alkyl, cycloalkyl, cycloalkylalkyl, heterocycloalkyl, heterocycloalkylalkyl, aryl, arylalkyl, heteroaryl, heteroarylalkyl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$) and —S(O)$_2$N(R$^{15}$)(R$^{16}$);

$R^{14}$ is 1-5 substituents independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

$R^{15}$, $R^{16}$ and $R^{17}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, arylheterocycloalkyl, $R^{18}$-alkyl, $R^{18}$-cycloalkyl, $R^{18}$-cycloalkylalkyl, $R^{18}$-heterocycloalkyl, $R^{18}$-heterocycloalkylalkyl, $R^{18}$-aryl, $R^{18}$-arylalkyl, $R^{18}$-heteroaryl and $R^{18}$-heteroarylalkyl; or $R^{15}$, $R^{16}$ and $R^{17}$ are

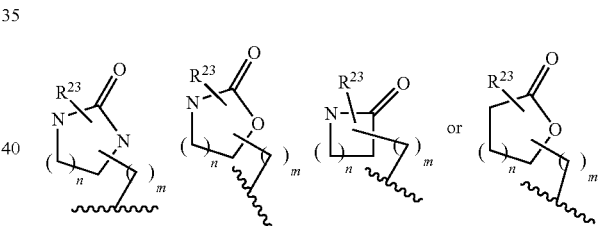

wherein $R^{23}$ numbers 0 to 5 substituents, m is 0 to 6 and n is 1 to 5;

$R^{18}$ is 1-5 substituents independently selected from the group consisting of alkyl, alkenyl, aryl, arylalkyl, arylalkenyl, arylalkynyl, —NO$_2$, halo, heteroaryl, HO-alkoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocycloalkyl), —S(O)$_2$N(alkyl)$_2$, —S(O)$_2$N(alkyl)(aryl), —OCF$_3$, —OH, —OR$^{20}$, —O-heterocycloalkyl, —O-cycloalkylalkyl, —O-heterocycloalkylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two $R^{18}$ moieties on adjacent carbons can be linked together to form

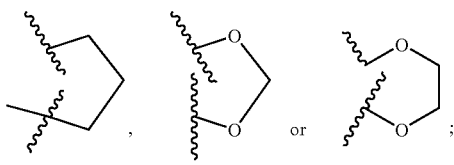

$R^{19}$ is alkyl, cycloalkyl, aryl, arylalkyl or heteroarylalkyl;

$R^{20}$ is alkyl, cycloalkyl, aryl, halo substituted aryl, arylalkyl, heteroaryl or heteroarylalkyl;

and wherein each of the arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl groups in $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently unsubstituted or substituted by 1 to 5 $R^{21}$ groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —$OR^{15}$, —$C(O)R^{15}$, —$C(O)OR^{15}$, —$C(O)N(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$R^{15}$; —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, =$NOR^{15}$, —$N_3$, —$NO_2$ and —$S(O)_2R^{15}$;

and wherein each of the alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{21}$ are independently unsubstituted or substituted by 1 to 5 $R^{22}$ groups independently selected from the group consisting of alkyl, cycloalkyl, cycloalkenyl, heterocycloalkyl, aryl, heteroaryl, halo, —$CF_3$, —CN, —$OR^{15}$, —$C(O)R^{15}$, —$C(O)OR^{15}$, -alkyl-$C(O)OR^{15}$, $C(O)N(R^{15})(R^{16})$, —$SR^{15}$, —$S(O)N(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$N_3$, =$NOR^{15}$, —$NO_2$, —$S(O)R^{15}$ and —$S(O)_2R^{15}$;

or two $R^{21}$ or two $R^{22}$ moieties on adjacent carbons can be linked together to form

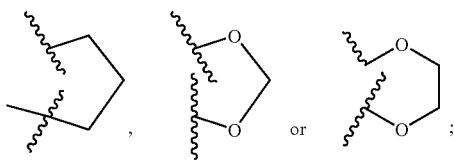

and when $R^{21}$ or $R^{22}$ are selected from the group consisting of —$C(=NOR^{15})R^{16}$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$ and —$CH_2$—$N(R^{15})C(O)OR^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by $R^{23}$;

$R^{23}$ is 1 to 5 groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —$OR^{24}$, —$C(O)R^{24}$, —$C(O)OR^{24}$, —$C(O)N(R^{24})(R^{25})$, —$SR^{24}$, —$S(O)N(R^{24})(R^{25})$, —$S(O)_2N(R^{24})(R^{25})$, —$C(=NOR^{24})R^{25}$, —$P(O)(OR^{24})(OR^{25})$, —$N(R^{24})(R^{25})$, -alkyl-$N(R^{24})(R^{25})$, —$N(R^{24})C(O)R^{25}$, —$CH_2$—$N(R^{24})C(O)R^{25}$, —$N(R^{24})S(O)R^{25}$, —$N(R^{24})S(O)_2R^{25}$, —$CH_2$—$N(R^{24})S(O)_2R^{25}$, —$N(R^{24})S(O)_2N(R^{25})(R^{26})$, —$N(R^{24})S(O)N(R^{25})(R^{26})$, —$N(R^{24})C(O)N(R^{25})(R^{26})$, —$CH_2$—$N(R^{24})C(O)N(R^{25})(R^{26})$, —$N(R^{24})C(O)OR^{25}$, —$CH_2$—$N(R^{24})C(O)OR^{25}$, —$S(O)R^{24}$ and —$S(O)_2R^{24}$; and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{23}$ are independently unsubstituted or substituted by 1 to 5 $R^{27}$ groups independently selected from the group consisting of alkyl, cycloalkyl, heterocycloalkyl, aryl, heteroaryl, halo, —$CF_3$, —CN, —$OR^{24}$, —$C(O)R^{24}$, —$C(O)OR^{24}$, alkyl-$C(O)OR^{24}$, —$C(O)N(R^{24})(R^{25})$, —$SR^{24}$, —$S(O)N(R^{24})(R^{25})$, —$S(O)_2N(R^{24})(R^{25})$, —$C(=NR^{24})R^{25}$, —$P(O)(OR^{24})(OR^{25})$, —$N(R^{24})(R^{25})$, -alkyl-$N(R^{24})(R^{25})$, —$N(R^{24})C(O)R^{25}$, —$CH_2$—$N(R^{24})C(O)R^{25}$, —$N(R^{24})S(O)R^{25}$, —$N(R^{24})S(O)_2R^{25}$, —$CH_2$—$N(R^{24})S(O)_2R^{25}$, —$N(R^{24})S(O)_2N(R^{25})(R^{26})$, —$N(R^{24})S(O)N(R^{25})(R^{26})$, —$N(R^{24})C(O)N(R^{25})(R^{26})$, —$CH_2$—$N(R^{24})C(O)N(R^{25})(R^{26})$, —$N(R^{24})C(O)OR^{25}$, —$CH_2$—$N(R^{24})C(O)OR^{25}$, —$S(O)R^{24}$ and —$S(O)_2R^{24}$;

$R^{24}$, $R^{25}$ and $R^{26}$ are independently selected from the group consisting of H, alkyl, cycloalkyl, cycloalkylalkyl, heterocycloalkyl, heterocycloalkylalkyl, aryl, arylalkyl, heteroaryl, heteroarylalkyl, arylcycloalkyl, $R^{27}$-alkyl, $R^{27}$-cycloalkyl, $R^{27}$-cycloalkylalkyl, $R^{27}$-heterocycloalkyl, $R^{27}$-heterocycloalkylalkyl, $R^{27}$-aryl, $R^{27}$-arylalkyl, $R^{27}$-heteroaryl and $R^{27}$-heteroarylalkyl;

$R^{27}$ is 1-5 substituents independently selected from the group consisting of alkyl, aryl, arylalkyl, —$NO_2$, halo, —$CF_3$, —CN, alkyl-CN, —$C(O)R^{28}$, —$C(O)OH$, —$C(O)OR^{28}$, —$C(O)NHR^{29}$, —$C(O)N(alkyl)_2$, —$C(O)N(alkyl)(aryl)$, —$C(O)N(alkyl)(heteroaryl)$, —$SR^{28}$, —$S(O)_2R^{29}$, —$S(O)NH_2$, —$S(O)NH(alkyl)$, —$S(O)N(alkyl)(alkyl)$, —$S(O)NH(aryl)$, —$S(O)_2NH_2$, —$S(O)_2NHR^{28}$, —$S(O)_2NH(aryl)$, —$S(O)_2NH(heterocycloalkyl)$, —$S(O)_2N(alkyl)_2$, —$S(O)_2N(alkyl)(aryl)$, —OH, —$OR^{29}$, —O-heterocycloalkyl, —O-cycloalkylalkyl, —O-heterocycloalkylalkyl, —$NH_2$, —$NHR^{29}$, —$N(alkyl)_2$, —$N(arylalkyl)_2$, —$N(arylalkyl)(heteroarylalkyl)$, —$NHC(O)R^{29}$, —$NHC(O)NH_2$, —$NHC(O)NH(alkyl)$, —$NHC(O)N(alkyl)(alkyl)$, —$N(alkyl)C(O)NH(alkyl)$, —$N(alkyl)C(O)N(alkyl)(alkyl)$, —$NHS(O)_2R^{29}$, —$NHS(O)_2NH(alkyl)$, —$NHS(O)_2N(alkyl)(alkyl)$, —$N(alkyl)S(O)_2NH(alkyl)$ and —$N(alkyl)S(O)_2N(alkyl)(alkyl)$;

$R^{28}$ is alkyl, cycloalkyl, arylalkyl or heteroarylalkyl; and $R^{29}$ is alkyl, cycloalkyl, aryl, arylalkyl, heteroaryl or heteroarylalkyl.

In another aspect, the invention relates to a pharmaceutical composition comprising at least one compound of formula I and a pharmaceutically acceptable carrier.

In another aspect, the invention comprises the method of inhibiting aspartyl protease comprising administering at least one compound of formula I to a patient in need of such treatment.

More specifically, the invention comprises: the method of treating a cardiovascular disease such as hypertension, renal failure, or a disease modulated by renin inhibition; the method of treating Human Immunodeficiency Virus; the method of treating a cognitive or neurodegenerative disease such as Alzheimer's Disease; the method of inhibiting plasmepins I and II for treatment of malaria; the method of inhibiting Cathepsin D for the treatment of Alzheimer's Disease, breast cancer, and ovarian cancer; and the method of inhibiting protozoal enzymes, for example inhibition of plasmodium falciparnum, for the treatment of fungal infections. Said method of treatment comprises administering at least one compound of formula I to a patient in need of such treatment. In particular, the invention comprises the method of treating Alzheimer's disease comprising administering at least one compound of formula I to a patient in need of such treatment.

In another aspect, the invention comprises the method of treating Alzheimer's disease comprising administering to a patient I need of such treatment a combination of at least one compound of formula I and a cholinesterase inhibitor or a muscarinic antagonist.

In a final aspect, the invention relates to a kit comprising in separate containers in a single package pharmaceutical compositions for use in combination, in which one container comprises a compound of formula I in a pharmaceutically acceptable carrier and a second container comprises a cholinesterase inhibitor or a muscarinic antagonist in a pharmaceutically acceptable carrier, the combined quantities being an effective amount to treat a cognitive disease or neurodegenerative disease such as Alzheimer's disease.

DETAILED DESCRIPTION

More preferred compounds of the invention are those of formula I wherein W is —C(O)—.

Another group of preferred compounds of formula I is that group wherein $R^1$ is alkyl, $R^2$ is H and $R^5$ is H, or even more preferably wherein $R^1$ is methyl.

In a group of preferred compounds of formula I is that group wherein $R^3$ and $R^6$, or $R^4$ and $R^7$, together with the carbon atoms to which they are attached form:

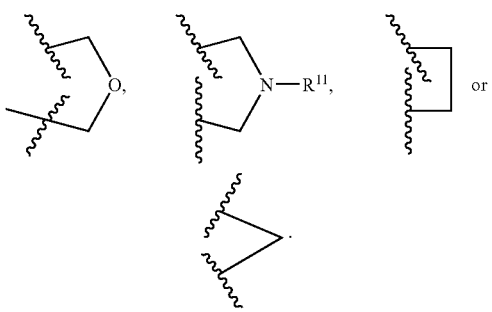

In a group of preferred compounds of formula I is that group wherein $R^3$ and $R^4$ or $R^6$ and $R^7$, together with the carbon atom to which they are attached form:

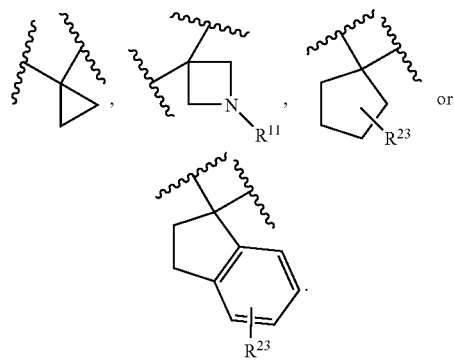

In a group of preferred compounds of formula I $R^{14}$ is aryl, heteroaryl, alkyl, cycloalkyl or cycloalkylalkyl.

In an additional group of preferred compounds of formula I $R^3$ or $R^4$ is methyl.

In an additional group of preferred compounds of formula I are those compounds wherein $R^1$ is alkyl;

$R^2$ is H or alkyl;

$R^3$ is H, aryl, heteroaryl, alkyl, cycloalkyl or cycloalkylalkyl;

$R^4$ is H or alkyl;

$R^5$ is H;

$R^{11}$ is H, aryl, heteroaryl, alkyl, cycloalkyl, cycloalkylalkyl, —C(O)$R^8$, —C(O)O$R^9$, —S(O)$_2R^{10}$, —C(O)N($R^{15}$)($R^{16}$) or —S(O)$_2$N($R^{15}$)($R^{16}$);

$R^{14}$ is aryl, heteroaryl, alkyl, cycloalkyl or cycloalkylalkyl; and

W is —C(O)—.

A further preferred group of compounds are those compounds of formula I with the following structures:

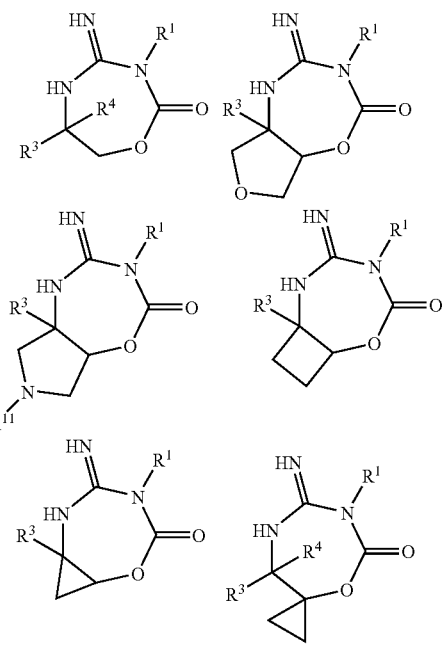

-continued

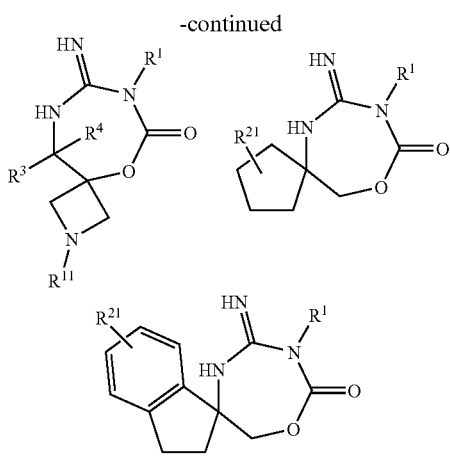

wherein $R^1$, $R^3$, $R^4$, $R^{14}$ and $R^{21}$ are defined above.

In an additional group of preferred compounds of formula I are those compounds wherein $R^3$ is aryl-substituted aryl, heteroaryl-substituted aryl, aryl-substituted heteroaryl or heteroaryl-substituted heteroaryl, aryl-substituted cycloalkyl, heteroaryl-substituted cycloalkyl, aryl-substituted alkyl, heteroaryl-substituted alkyl, aryl-substituted cycloalkyl or heteroaryl-substituted cycloalkylalkyl.

In an additional group of preferred compounds of formula I are those compounds wherein $R^3$ is

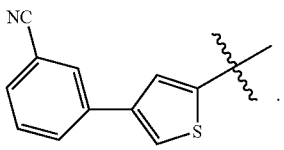

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. The alkyl group can be optionally substituted with one or more substituents (e.g., $R^{18}$, $R^{21}$ $R^{22}$, etc.) which may be the same or different, and are as defined herein. Substituted alkyl groups include fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more substituents (e.g., $R^{18}$, $R^{21}$, $R^{22}$, etc.) which may be the same or different, and are as defined herein or two substituents on adjacent carbons can be linked together to form

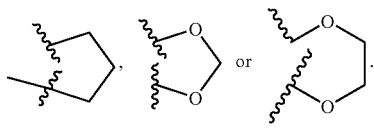

Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one to four of the ring atoms is an element other than carbon, for example nitrogen, oxygen or sulfur, alone or in combination. Preferred heteroaryls contain about 5 to about 6 ring atoms. The "heteroaryl" group can be optionally substituted with one or more substituents (e.g., $R^{18}$, $R^{21}$, $R^{22}$, etc.) which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b] thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl group can be optionally substituted with one or more substituents (e.g., $R^{18}$, $R^{21}$, $R^{22}$, etc.) which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Further non-limiting examples of cycloalkyl include the following

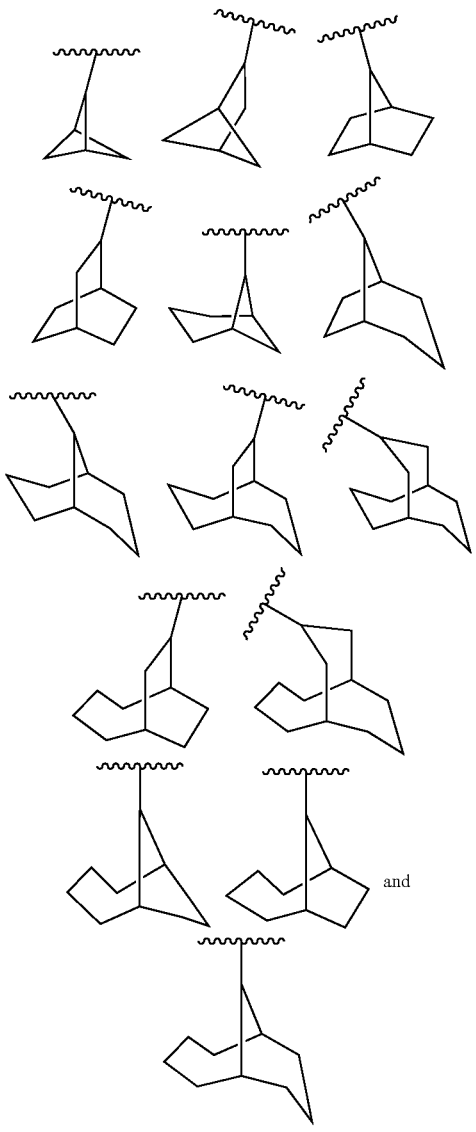

and

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkenyl" means a non-aromatic mono or multicyclic ring system comprising about 3 to about 10 carbon atoms, preferably about 5 to about 10 carbon atoms which contains at least one carbon-carbon double bond. The cycloalkenyl ring can be optionally substituted with one or more substituents (e.g., $R^{18}$, $R^{21}$, $R^{22}$, etc.) which may be the same or different, and are as defined herein. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl group can be optionally substituted with one or more substituents (e.g., $R^{18}$, $R^{21}$, $R^{22}$, etc.) which may be the same or different, and are as defined herein. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Heterocyclyl" (or heterocycloalkyl) means a non-aromatic saturated monocyclic or multicyclic ring system comprising about 3 to about 10 ring atoms, preferably about 5 to about 10 ring atoms, in which 1-3, preferably 1 or 2 of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl group can be optionally substituted with one or more substituents (e.g., $R^{18}$, $R^{21}$, $R^{22}$, etc.) which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be group can be optionally substituted with one or more substituents (e.g., R$^{18}$, R$^{21}$, R$^{22}$, etc.) which may be the same or different, and are as defined herein. For example, the arylcycloalkyl group can be optionally substituted by 1-5 R$^{21}$ groups. Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylhetercycloalkyl group can be optionally substituted with one or more substituents (e.g., R$^{18}$, R$^{21}$, R$^{22}$, etc.) which may be the same or different, and are as defined herein. For example, the arylheterocycloalkyl can be optionally substituted by 1-5 R$^{21}$ substituents. Non-limiting examples of suitable arylheterocycloalkyls include

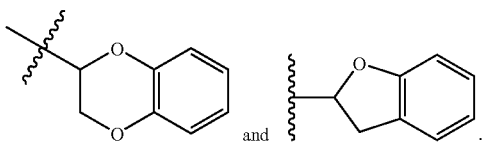

and

The bond to the parent moiety is through a non-aromatic carbon atom.

Similarly, "heteroarylalkyl" "cycloalkylalkyl" and "heterocycloalkylalkyl" mean a heteroaryl-, cycloalkyl- or heterocycloalkyl-alkyl- group in which the heteroaryl, cycloalkyl, heterocycloalkyl and alkyl are as previously described. Preferred groups contain a lower alkyl group. The bond to the parent moiety is through the alkyl.

"Acyl" means an H—C(O)—, alkyl-C(O)—, alkenyl-C(O)—, alkynyl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkyoxyalkyl" means a group derived from an alkoxy and alkyl as defined herein. The bond to the parent moiety is through the alkyl.

"Arylalkenyl" means a group derived from an aryl and alkenyl as defined herein. Preferred arylalkenyls are those wherein aryl is phenyl and the alkenyl consists of about 3 to about 6 atoms. The arylalkenyl group can be optionally substituted with one or more substituents (e.g., R$^{18}$, R$^{21}$, R$^{22}$, etc.) which may be the same or different, and are as defined herein. For example, the arylalkenyl can be optionally substituted by one or more R substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl group can be optionally substituted with one or more substituents (e.g., R$^{18}$, R$^{21}$, R$^{22}$, etc.) which may be the same or different, and are as defined herein. For example, the arylalkynyl can be optionally substituted by one or more R$^{21}$ substituents. The bond to the parent moiety is through a non-aromatic carbon atom.

The suffix "ene" on alkyl, aryl, hetercycloalkyl, etc. indicates a divalent moiety, e.g., —CH$_2$CH$_2$— is ethylene, and

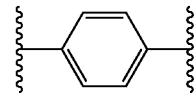

is para-phenylene.

The term "optionally substituted" means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, e.g., R$^8$ in —N(R$^8$)$_2$, or a variable appears more than once in the structure of formula I, e.g., R$^{15}$ may appear in both R$^1$ and R$^3$, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ∿∿∿ as a bond generally indicates a mixture of, or either of, the possible isomers, e.g., containing (R)— and (S)— stereochemistry. For example,

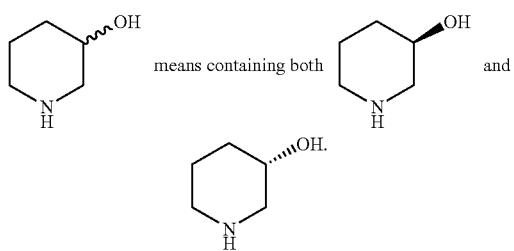

means containing both and

Lines drawn into the ring systems, such as, for example:

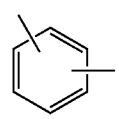

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

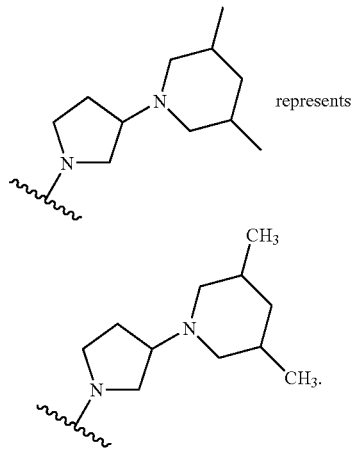

It should also be noted that any heteroatom with unsatisfied valences in the text, schemes, examples, structural formulae, and any Tables herein is assumed to have the hydrogen atom or atoms to satisfy the valences.

Those skilled in the art will recognize that certain compounds of formula I are tautomeric, and all such tautomeric forms are contemplated herein as part of the present invention. For example, a compound wherein $R^1$ and $R^5$ are each H can be represented by any of the following structures:

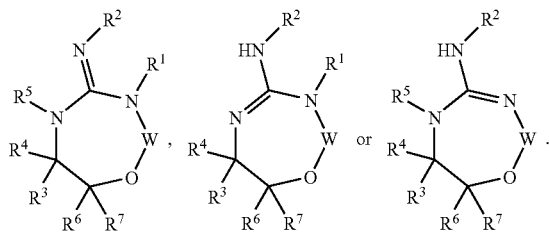

When $R^{21}$ and $R^{22}$, are, for example, —N($R^{15}$)C(O)N($R^{16}$)($R^{17}$) and $R^{15}$ and $R^{16}$ form a ring, the moiety formed, is, for example,

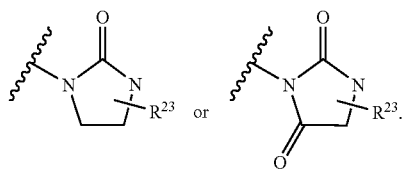

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting aspartyl protease and/or inhibiting BACE-1 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt (s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, bisulfates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as 2H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The compounds according to the invention have pharmacological properties; in particular, the compounds of Formula I can be aspartyl protease inhibitors.

Compounds of formula I can be made using procedures known in the art. The following reaction schemes show typical procedures, but those skilled in the art will recognize that other procedures can also be suitable.

In the Schemes and in the Example below, the following abbreviations are used:

r.t. or R.T.: room temperature
eq: equivalent
aq.: aqueous
Boc: tert-butoxycarbonyl
TFA: trifluoroacetic acid
DCM: dichloromethane
DMF: N,N-dimethylformamide
MeI: methyl iodide
PhI(OAc)$_2$: Iodobenzene diacetate
Rh$_2$(OAc)$_4$: Rhodium (II) acetate
Pd(PPh$_3$)$_4$: tetrakis (Triphenylphosphine) Palladium
THF: Tetrahydrofuran
min: minute
mL: milliliter
sat.: saturated The compounds in the invention may be produced by processes known to those skilled in the art and as shown in the following reaction schemes and in the preparations and examples described below.

EXPERIMENTAL EXAMPLES

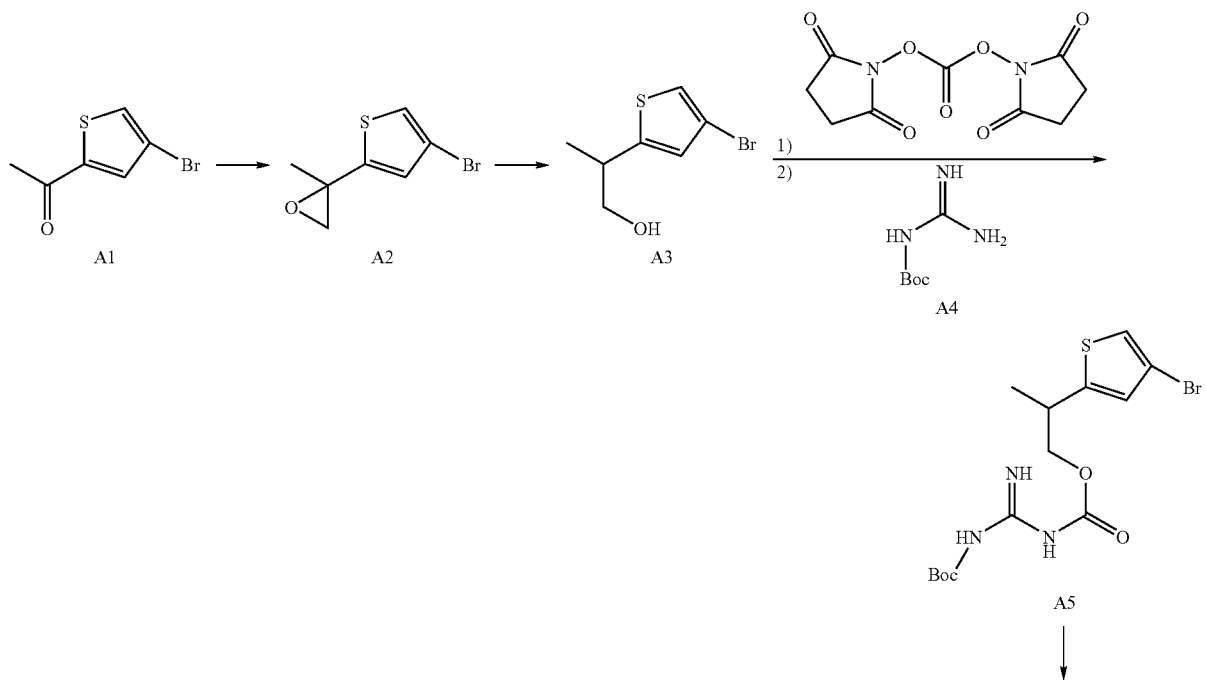

-continued

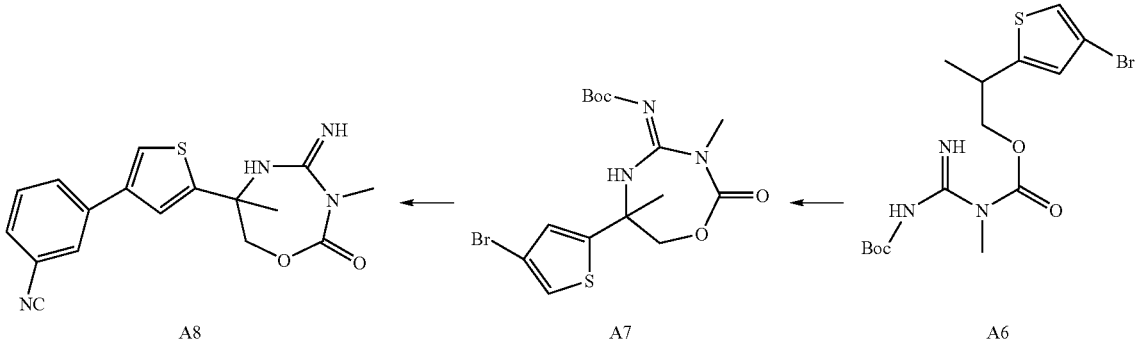

Method A, Step 1;

To a acetonitrile solution of A1 (1 mmol) is added trimethylsulfonium iodide (1.1 eq) and 1N aq KOH (1.1 eq) and the reaction is stirred overnight. The reaction mixture is partitioned between DCM/water. The organic layer is dried and solvent evaporated and the residue is chromatographed to give compound A2.

Method A, Step 2;

To a 10 ml DCM solution of A2 (1 mmol) and triethylsilane (2 eq) is added 5 ml of TFA and reaction is stirred until the A2 disappears. The solvent is removed to give product A3.

Method A, Step 3;

To an anhydrous DCM solution of A3 is added bis(N-hydroxysuccimide)carbonate (1 eq) and the solution is stirred until A3 disappears before N-boc-guanidine (A4, 1 eq) is added. The reaction is stirred overnight before it is washed with aq NaHCO₃ and brine. The organic layer is dried, its solvent is removed and the residue is chromatographed to give A5.

Method A, Step 4;

To a DMF solution of A5 is added 1 eq of MeI and 1N Na₂CO₃ and the mixture is stirred overnight before it is partitioned between DCM/Water. The organic layer is dried and solvent evaporated and the residue chromatographed to give A6.

Method A, Step 5;

A literature procedure is adapted (C. Espino and J. Du Bois; *Angew. Chem. Int. Ed.* 2001, 40, 598).

A mixture of A6 (5 mmol), PhI(OAc)₂ (1.4 eq), MgO (2.4 eq) and Rh₂(OAc)₄ (0.05%) is stirred at r.t. overnight to give product A7 after purification.

Method A, Step 6.

A mixture of A7 (1 mmol) in 4 ml of DMF, m-Cyanophenylboronic acid (1.1 eq), sat. aq K₂CO₃ (2 eq) and Pd(PPh₃)₄ (10%) is heated under nitrogen to 100° C. for 10 min using a microwave oven. The reaction mixture is purified and the product is treated with 40% TFA in DCM to afford compound A8.

Method B

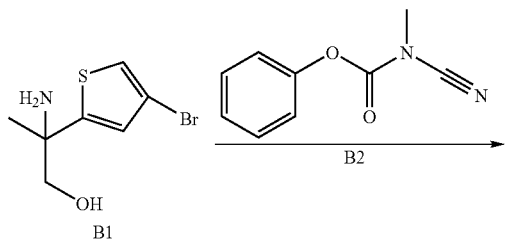

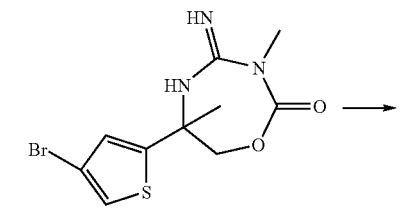

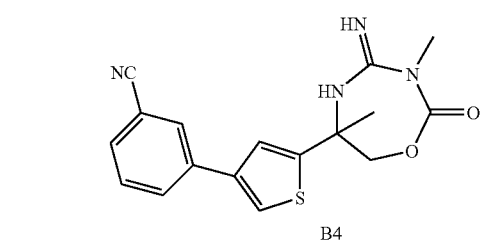

Method B, Step 1

To a acetonitrile solution of A2 is added aq 1N NaN₃ (2 eq) tetrabutylammonium bromide (2 eq). The mixture is stirred overnight before it is partitioned between DCM/water. The organic layer is dried, solvent evaporated and residue purified to give the azide which is reduced to aminoalcohol using polystyrene bound triphenylphosphine in wet THF to give a crude produce B1 which is used without purification.

Method B, Step 2;

To a acetonitrile solution of B1 is added B2, which is produced using a known literature procedure (*Zeitschrift fure Anorganische und Allgemeine Chemie*, 505, 171-9; 1983) and the solution is heated to 100° C. in a microwave oven for 5 min before the solvent is evaporated and residue purified to give B3.

Method B, Step 3.

A mixture of B3 (1 mmol) in 4 ml of DMF, m-Cyanophenylboronic acid (1.1 eq), sat. aq $K_2CO_3$ (2 eq) and $Pd(PPh_3)_4$ (10%) is heated under nitrogen to 100° C. for 10 min using a microwave oven. The reaction mixture is purified and the product is treated with 40% TFA in DCM to afford compound B4 after purification.

Human Cathepsin D FRET Assay

This assay can be run in either continuous or endpoint format. The substrate used below has been described (Y. Yasuda et al., J. Biochem., 125, 1137 (1999)). Substrate and enzyme are commercially available. A Km of 4 uM was determined in our lab for the substrate below under the assay conditions described and is consistent with Yasuda et al.

The assay is run in a 30 ul final volume using a 384 well Nunc black plate. 8 concentrations of compound are pre-incubated with enzyme for 30 mins at 37 C followed by addition of substrate with continued incubation at 37 C for 45 mins. The rate of increase in fluorescence is linear for over 1 h and is measured at the end of the incubation period using a Molecular Devices FLEX station plate reader. Kis are interpolated from the IC50s using a Km value of 4 uM and the substrate concentration of 2.5 uM.

Reagents
Na-Acetate pH 5
1% Brij-35 from 10% stock (Calbiochem)
DMSO
Purified (>95%) human liver Cathepsin D (Athens Research & Technology Cat# 16-12-030104)
Peptide substrate(Km=4 uM) Bachem Cat # M-2455
Pepstatin is used as a control inhibitor (Ki~0.5 nM) and is available from Sigma.
Nunc 384 well black plates Final Assay buffer conditions
100 mM Na Acetate pH 5.0
0.02% Brij-35
1% DMSO Compound is diluted to 3× final concentration in assay buffer containing 3% DMSO. 10 ul of compound is added to 10 ul of 2.25 nM enzyme(3×) diluted in assay buffer without DMSO, mixed briefly, spun, and incubated at 37 C for 30 mins. 3× substrate (7.5 uM) is prepared in 1× assay buffer without DMSO. 10 ul of substrate is added to each well mixed and spun briefly to initiate the reaction. Assay plates are incubated at 37 C for 45 mins and read on 384 compatible fluorescence plate reader using a 328 nm Ex and 393 nm Em.

BACE-1 Cloning, Protein Expression and Purification

A predicted soluble form of human BACE1 (sBACE1, corresponding to amino acids 1-454) was generated from the full length BACE1 cDNA (full length human BACE1 cDNA in pCDNA4/mycHisA construct; University of Toronto) by PCR using the advantage-GC cDNA PCR kit (Clontech, Palo Alto, Calif.). A HindIII/PmeI fragment from pCDNA4-sBACE1myc/His was blunt ended using Klenow and subcloned into the Stu I site of pFASTBACI(A) (Invitrogen). A sBACE1 mycHis recombinant bacmid was generated by transposition in DH10Bac cells(GIBCO/BRL). Subsequently, the sBACE1 mycHis bacmid construct was transfected into sf9 cells using CellFectin (Invitrogen, San Diego, Calif.) in order to generate recombinant baculovirus. Sf9 cells were grown in SF 900-II medium (Invitrogen) supplemented with 3% heat inactivated FBS and 0.5× penicillin/streptomycin solution (Invitrogen). Five milliliters of high titer plaque purified sBACEmyc/His virus was used to infect 1 L of logarithmically growing sf9 cells for 72 hours. Intact cells were pelleted by centrifugation at 3000×g for 15 minutes. The supernatant, containing secreted sBACE1, was collected and diluted 50% v/v with 100 mM HEPES, pH 8.0. The diluted medium was loaded onto a Q-sepharose column. The Q-sepharose column was washed with Buffer A (20 mM HEPES, pH 8.0, 50 mM NaCl).

Proteins, were eluted from the Q-sepharose column with Buffer B (20 mM HEPES, pH 8.0, 500 mM NaCl). The protein peaks from the Q-sepharose column were pooled and loaded onto a Ni-NTA agarose column. The Ni-NTA column was then washed with Buffer C (20 mM HEPES, pH 8.0, 500 mM NaCl). Bound proteins were then eluted with Buffer D (Buffer C+250 mM imidazole). Peak protein fractions as determined by the Bradford Assay (Biorad, CA) were concentrated using a Centricon 30 concentrator (Millipore). sBACE1 purity was estimated to be ~90% as assessed by SDS-PAGE and Commassie Blue staining. N-terminal sequencing indicated that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin; CIS-Bio International, France), 5 μM unlabeled APPsw peptide (KTEEISEVNLDAEFRHDK; American Peptide Company, Sunnyvale, Calif.), 7 nM sproBACE1, 20 mM PIPES pH 5.0, 0.1%Brij-35 (protein grade, Calbiochem, San Diego, Calif.), and 10% glycerol were preincubated for 30 min at 30° C. Reactions were initiated by addition of substrate in a 5 μl aliquot resulting in a total volume of 25 μl. After 3 hr at 30° C. reactions were terminated by addition of an equal volume of 2× stop buffer containing 50 mM Tris-HCl pH 8.0, 0.5 M KF, 0.001% Brij-35, 20 μg/ml SA-XL665 (cross-linked allophycocyanin protein coupled to streptavidin; CIS-Bio International, France) (0.5 μg/well). Plates were shaken briefly and spun at 1200×g for 10 seconds to pellet all liquid to the bottom of the plate before the incubation. HTRF measurements were made on a Packard Discovery® HTRF plate reader using 337 nm laser light to excite the sample followed by a 50 μs delay and simultaneous measurements of both 620 nm and 665 nm emissions for 400 μs.

$IC_{50}$ determinations for inhibitors, (I), were determined by measuring the percent change of the relative fluorescence at 665 nm divided by the relative fluorescence at 620 nm, (665/620 ratio), in the presence of varying concentrations of I and a fixed concentration of enzyme and substrate. Nonlinear regression analysis of this data was performed using Graph-Pad Prism 3.0 software selecting four parameter logistic equation, that allows for a variable slope. Y=Bottom+(Top-Bottom)/(1+10^((LogEC50-X)*Hill Slope)); X is the logarithm of concentration of I, Y is the percent change in ratio and Y starts at bottom and goes to top with a sigmoid shape.

Human Mature Renin Enzyme Assay:

Human Renin was cloned from a human kidney cDNA library and C-terminally epitope-tagged with the V5-6His sequence into pCDNA3.1. pCNDA3.1-Renin-V5-6His was stably expressed in HEK293 cells and purified to >80% using standard Ni-Affinity chromatography. The prodomain of the recombinant human renin-V5-6His was removed by limited proteolysis using immobilized TPCK-trypsin to give mature-human renin. Renin enzymatic activity was monitored using a commercially available fluorescence resonance energy transfer(FRET) peptide substrate,RS-1(Molecular Probes, Eugene, Oreg.) in 50 mM Tris-HCl pH 8.0, 100 mM NaCl, 0.1%Brij-35 and 5% DMSO buffer for 40 mins at 30 degrees celsius in the presence or absence of different concentrations of test compounds. Mature human Renin was present at approximately 200 nM. Inhibitory activity was defined as the percent decrease in renin induced fluorescence at the end of the 40 min incubation compared to vehicle controls and samples lacking enzyme.

In the aspect of the invention relating to a combination of a compound of formula I with a cholinesterase inhibitor, acetyl- and/or butyrylchlolinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred.

In the aspect of the invention relating to a combination of a compound of formula I with a muscarinic antagonist, $m_1$ or $m_2$ antagonists can be used. Examples of $m_1$ antagonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

When a compound of formula I is used in combination with a cholinesterase inhibitor to treat cognitive disorders, these two active components may be co-administered simultaneously or sequentially, or a single pharmaceutical composition comprising a compound of formula I and a cholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the cholinesterase inhibitor can be determined from published material, and may range from 0.001 to 100 mg/kg body weight.

When separate pharmaceutical compositions of a compound of formula I and a cholinesterase inhibitor are to be administered, they can be provided in a kit comprising in a single package, one container comprising a compound of formula I in a pharmaceutically acceptable carrier, and a separate container comprising a cholinesterase inhibitor in a pharmaceutically acceptable carrier, with the compound of formula I and the cholinesterase inhibitor being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound having the structural formula

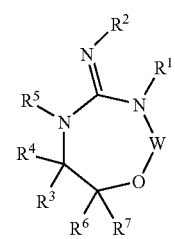

I or an isomer, pharmaceutically acceptable salt of said compound or said isomer, wherein W is —S(O)—, —S(O)$_2$—, —P(O)(OR$^{15}$)— or —C(═O)—;

R$^1$, R$^2$ and R$^5$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —OR$^{15}$, —CN, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^8$)$_2$;

R$^3$, R$^4$, R$^6$ and R$^7$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl, —CH$_2$—O—Si(R$^9$)(R$^{10}$)(R$^{19}$), —CN, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$, —N(R$^{11}$)C(O)N(R$^{12}$)(R$^{13}$), —N(R$^{11}$)C(O)OR$^9$ and —C(=NOH)R$^8$;

or optionally, any two of R$^3$, R$^4$, R$^6$ and R$^7$ together with the carbon atoms to which they are attached form:

a) a 3- to 8-membered cycloalkyl ring optionally substituted by 1 to 5 R$^{23}$ moieties; and b) 1-4 of the atoms in the above 3-8 membered cycloalkyl ring can be replaced by —O—, —S—, —N(R$^{11}$)—, —C(O)—, —S(O)— or —S(O)$_2$—;

R$^8$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

R$^9$ is independently selected from the group consisting of H, alkyl, cycloalkyl, cycloalkylalkyl, heterocycloalkyl, heterocycloalkylalkyl, aryl, arylalkyl, heteroaryl and heteroarylalkyl;

R$^{10}$ is independently selected from the group consisting of H, alkyl, alkenyl, cycloalkyl, cycloalkylalkyl, cycloalkenyl, heterocycloalkyl, heterocycloalkylalkyl, aryl, arylalkyl, heteroaryl, heteroarylalkyl and —N(R$^{15}$)(R$^{16}$);

R$^{11}$, R$^{12}$ and R$^{13}$ are independently selected from the group consisting of H, alkyl, cycloalkyl, cycloalkylalkyl, heterocycloalkyl, heterocycloalkylalkyl, aryl, arylalkyl, heteroaryl, heteroarylalkyl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$) and —S(O)$_2$N(R$^{15}$)(R$^{16}$);

R$^{14}$ is 1-5 substituents independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

R$^{15}$, R$^{16}$ and R$^{17}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, arylheterocycloalkyl, R$^{18}$-alkyl, R$^{18}$-cycloalkyl, R$^{18}$-cycloalkylalkyl, R$^{18}$-heterocycloalkyl, R$^{18}$-heterocycloalkylalkyl, R$^{18}$-aryl, R$^{18}$-arylalkyl, R$^{18}$-heteroaryl and R$^{18}$-heteroarylalkyl; or R$^{15}$, R$^{16}$ and R$^{17}$ are

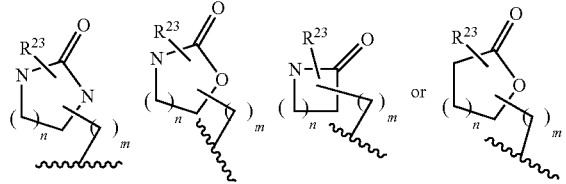

wherein R$^{23}$ numbers 0 to 5 substituents, m is 0 to 6 and n is 1 to 5;

R$^{18}$ is 1-5 substituents independently selected from the group consisting of alkyl, alkenyl, aryl, arylalkyl, arylalkenyl, arylalkynyl, —NO$_2$, halo, heteroaryl, HO-alkoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocycloalkyl), —S(O)$_2$N(alkyl)$_2$, —S(O)$_2$N(alkyl)(aryl), —OCF$_3$, —OH, —OR$^{20}$, —O-heterocycloalkyl, —O-cycloalkylalkyl, —O-heterocycloalkylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two R$^{18}$ moieties on adjacent carbons can be linked together to form

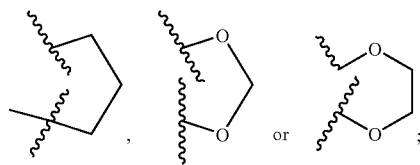

R$^{19}$ is alkyl, cycloalkyl, aryl, arylalkyl or heteroarylalkyl;

R$^{20}$ is alkyl, cycloalkyl, aryl, halo substituted aryl, arylalkyl, heteroaryl or heteroarylalkyl;

and wherein each of the arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl, heterocycloalkenylaryl groups in $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently unsubstituted or substituted by 1 to 5 $R^{21}$ groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —$OR^{15}$, —$C(O)R^{15}$, —$C(O)OR^{15}$, —$C(O)N(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl -$N(R^{15})(R^{16})$, —$N(R^{15})C(O)R^{16}$, —$CH_2$—$N(R^{15})C(O)R^{16}$, —$CH_2$—$R^{15}$; —$N(R^{15})S(O)R^{16}$, —$N(R^{15})S(O)_2R^{16}$, —$CH_2$—N$(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, =$NOR^{15}$, —$N_3$, —$NO_2$ and —$S(O)_2R^{15}$; and wherein each of the alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{21}$ are independently unsubstituted or substituted by 1 to 5 $R^{22}$ groups independently selected from the group consisting of alkyl, cycloalkyl, cycloalkenyl, heterocycloalkyl, aryl, heteroaryl, halo, —$CF_3$, —CN, —$OR^{15}$, —$C(O)R^{15}$, —$C(O)OR^{15}$, -alkyl-$C(O)OR^{15}$, $C(O)N(R^5)(R^{16})$, —$SR^{15}$, —$S(O)N(R^{15})(R^{16})$, —$S(O)_2N(R^{15})(R^{16})$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$N_3$, =$NOR^{15}$, —$NO_2$, —$S(O)R^{15}$ and —$S(O)_2R^{15}$;

or two $R^{21}$ or two $R^{22}$ moieties on adjacent carbons can be linked together to form

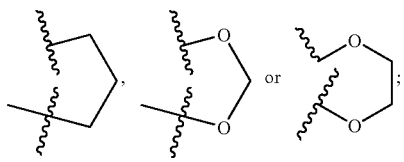

and when $R^{21}$ or $R^{22}$ are selected from the group consisting of —$C(=NOR^{15})R^{16}$, —$N(R^{15})C(O)R^{16}$, —$CH_2$—N$(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$ and —$CH_2$—$N(R^{15})C(O)OR^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by $R^{23}$;

$R^{23}$ is 1 to 5 groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —$OR^{24}$, —$C(O)R^{24}$, —$C(O)OR^{24}$, —$C(O)N(R^{24})(R^{25})$, —$SR^{24}$, —$S(O)N(R^{24})(R^{25})$, —$S(O)_2N(R^{24})(R^{25})$, —$C(=NOR^{24})R^{25}$, —$P(O)(OR^{24})(OR^{25})$, —$N(R^{24})(R^{25})$, -alkyl-$N(R^{24})(R^{25})$, —$N(R^{24})C(O)R^{25}$, —$CH_2$—$N(R^{24})C(O)R^{25}$, —$N(R^{24})S(O)R^{25}$, —$N(R^{24})S(O)_2R^{25}$, —$CH_2$—N$(R^{24})S(O)_2R^{25}$, —$N(R^{24})S(O)_2N(R^{25})(R^{26})$, —$N(R^{24})S(O)N(R^{25})(R^{26})$, —$N(R^{24})C(O)N(R^{25})(R^{26})$, —$CH_2$—$N(R^{24})C(O)N(R^{25})(R^{26})$, —$N(R^{24})C(O)OR^{25}$, —$CH_2$—$N(R^{24})C(O)OR^{25}$, —$S(O)R^{24}$ and —$S(O)_2R^{24}$; and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{23}$ are independently unsubstituted or substituted by 1 to 5 $R^{27}$ groups independently selected from the group consisting of alkyl, cycloalkyl, heterocycloalkyl, aryl, heteroaryl, halo, —$CF_3$, —CN, —$OR^{24}$, —$C(O)R^{24}$, —$C(O)OR^{24}$, alkyl -$C(O)OR^{24}$, —$C(O)N(R^{24})(R^{25})$, —$SR^{24}$, —$S(O)N(R^{24})(R^{25})$, —$S(O)_2N(R^{24})(R^{25})$, —$C(=NOR^{24})R^{25}$, —$P(O)(OR^{24})(OR^{25})$, —$N(R^{24})(R^{25})$, -alkyl-$N(R^{24})(R^{25})$, —$N(R^{24})C(O)R^{25}$, —$CH_2$—$N(R^{24})C(O)R^{25}$, —$N(R^{24})S(O)R^{25}$, —$N(R^{24})S(O)_2R^{25}$, —$CH_2$—N$(R^{24})S(O)_2R^{25}$, —$N(R^{24})S(O)_2N(R^{25})(R^{26})$, —$N(R^{24})S(O)N(R^{25})(R^{26})$, —$N(R^{24})C(O)N(R^{25})(R^{26})$, —$CH_2$—$N(R^{24})C(O)N(R^{25})(R^{26})$, —$N(R^{24})C(O)OR^{25}$, —$CH_2$—$N(R^{24})C(O)OR^{25}$, —$S(O)R^{24}$ and —$S(O)_2R^{24}$;

$R^{24}$, $R^{25}$ and $R^{26}$ are independently selected from the group consisting of H, alkyl, cycloalkyl, cycloalkylalkyl, heterocycloalkyl, heterocycloalkylalkyl, aryl, arylalkyl, heteroaryl, heteroarylalkyl, arylcycloalkyl, $R^{27}$-alkyl, $R^{27}$-cycloalkyl, $R^{27}$-cycloalkylalkyl, $R^{27}$-heterocycloalkyl, $R^{27}$-heterocycloalkylalkyl, $R^{27}$-aryl, $R^{27}$-arylalkyl, $R^{27}$-heteroaryl and $R^{27}$-heteroarylalkyl;

$R^{27}$ is 1-5 substituents independently selected from the group consisting of alkyl, aryl, arylalkyl, —$NO_2$, halo, —$CF_3$, —CN, alkyl-CN, —$C(O)R^{28}$, —$C(O)OH$, —$C(O)OR^{28}$, —$C(O)NHR^{29}$, —$C(O)N(alkyl)_2$, —$C(O)N(alkyl)(aryl)$, —$C(O)N(alkyl)(heteroaryl)$, —$SR^{28}$, —$S(O)_2R^{29}$, —$S(O)NH_2$, —$S(O)NH(alkyl)$, —$S(O)N(alkyl)(alkyl)$, —$S(O)NH(aryl)$, —$S(O)_2NH_2$, —$S(O)_2NHR^{28}$, —$S(O)_2NH(aryl)$, —$S(O)_2NH(heterocycloalkyl)$, —$S(O)_2N(alkyl)_2$, —$S(O)_2N(alkyl)(aryl)$, —OH, —$OR^{29}$, —O-heterocycloalkyl, —O-cycloalkylalkyl, —O-heterocycloalkylalkyl, —$NH_2$, —$NHR^{29}$, —$N(alkyl)_2$, —$N(arylalkyl)_2$, —$N(arylalkyl)(heteroarylalkyl)$, —$NHC(O)R^{29}$, —$NHC(O)NH_2$, —NHC(O)NH(alkyl), —NHC(O)N(alkyl)(alkyl), —N(alkyl)C(O)NH(alkyl), —N(alkyl)C(O)N(alkyl)(alkyl), —$NHS(O)_2R^{29}$, —$NHS(O)_2NH(alkyl)$, —$NHS(O)_2N(alkyl)(alkyl)$, —$N(alkyl)S(O)_2NH(alkyl)$ and —$N(alkyl)S(O)_2N(alkyl)(alkyl)$;

$R^{28}$ is alkyl, cycloalkyl, arylalkyl or heteroarylalkyl; and $R^{29}$ is alkyl, cycloalkyl, aryl, arylalkyl, heteroaryl or heteroarylalkyl, wherein "heteroaryl" means a group selected from pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1, 2-a]pyridinyl, imidazo[2,1-b]thiazolyl, benzofurazanyl, indolyl, azaindolyl, benzimidazolyl, benzothienyl, guinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl, wherein "heterocycloalkyl" means a group selected from piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl, and wherein "cycloalkyl" means a mono or multicyclic group selected from cyclopropyl, cyclopentyl, cyclohexyl, cycloheptyl, 1-decalin, norbornyl, adamantyl,

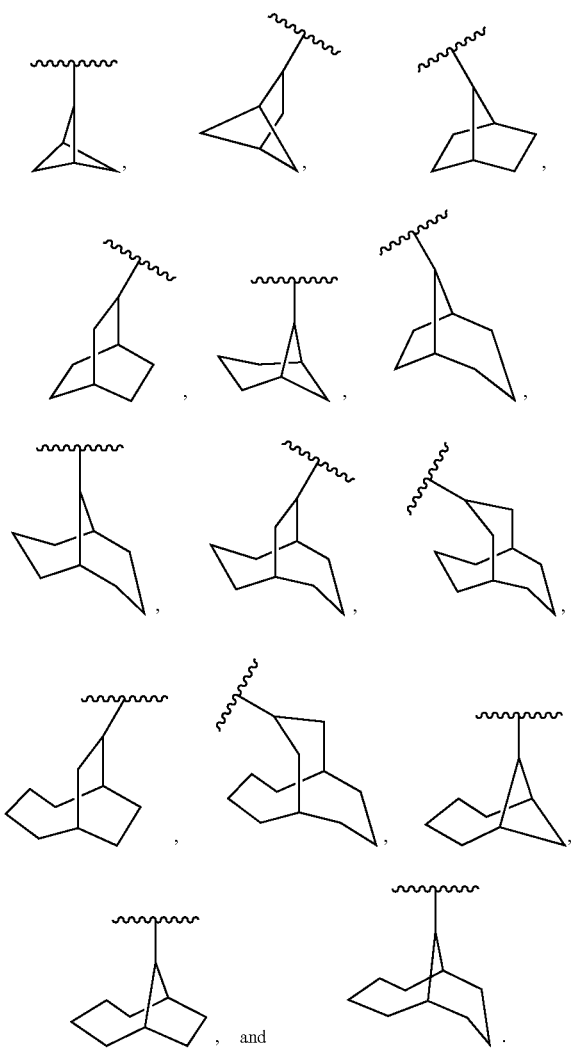

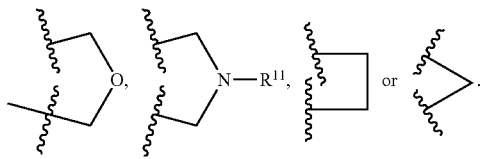

6. A compound of claim 1, or a pharmaceutically acceptable salt thereof, wherein $R^3$ and $R^4$ or $R^6$ and $R^7$, together with the carbon atom to which they are attached form:

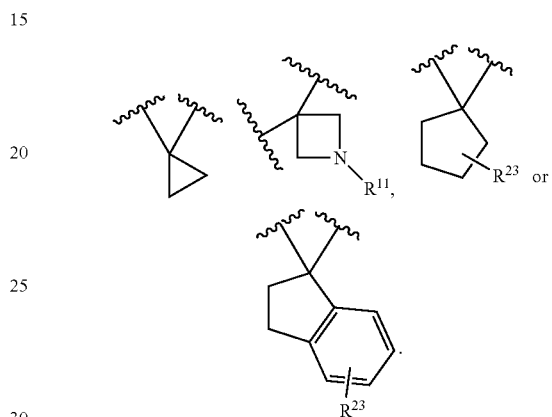

7. A compound of claim 1, or a pharmaceutically acceptable salt thereof, wherein $R^{14}$ is aryl, heteroaryl, alkyl, cycloalkyl or cycloalkylalkyl.

8. A compound of claim 1, or a pharmaceutically acceptable salt thereof, wherein $R^3$ or $R^4$ is methyl.

9. A compound of claim 1, or a pharmaceutically acceptable salt thereof, wherein $R^1$ is alkyl;

$R^2$ is H or alkyl;

$R^3$ is H, aryl, heteroaryl, alkyl, cycloalkyl or cycloalkylalkyl;

$R^4$ is H or alkyl;

$R^5$ is H;

$R^{11}$ is H, aryl, heteroaryl, alkyl, cycloalkyl, cycloalkylalkyl, —C(O)R$^8$, —C(O)OR$^9$, —S(O)$_2$R$^{10}$, —C(O)N(R$^{15}$)(R$^{16}$) or —S(O)$_2$N(R$^{15}$)(R$^{16}$);

$R^{14}$ is aryl, heteroaryl, alkyl, cycloalkyl or cycloalkylalkyl; and

W is —C(O)—.

2. A compound of claim 1, or a pharmaceutically acceptable salt thereof, wherein W is —C(O)—.

3. A compound of claim 1, or a pharmaceutically acceptable salt thereof, wherein $R^1$ is alkyl, $R^2$ is H and $R^5$ is H.

4. A compound of claim 3, or a pharmaceutically acceptable salt thereof, where $R^1$ is methyl.

5. A compound of claim 1, or a pharmaceutically acceptable salt thereof, wherein $R^3$ and $R^6$, or $R^4$ and $R^7$, together with the carbon atoms to which they are attached form:

10. A compound of claim 1, or a pharmaceutically acceptable salt thereof, selected from the following structures:

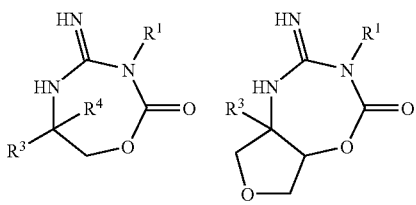

-continued

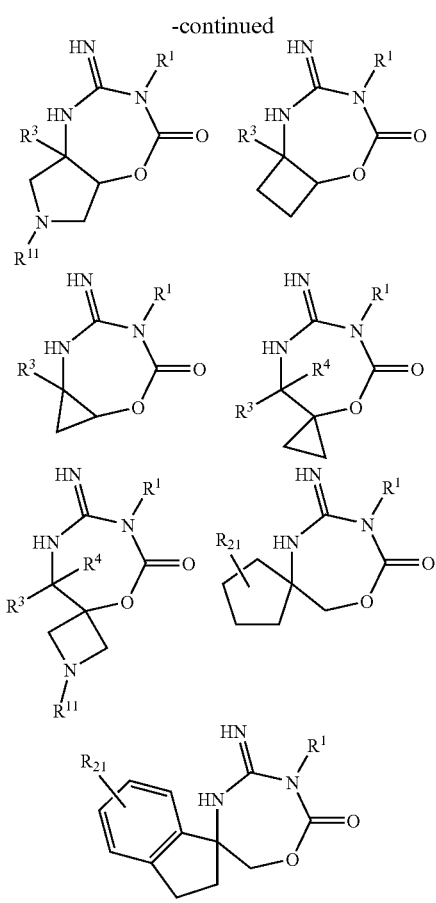

wherein $R^1$, $R^3$, $R^4$, $R^{14}$ and $R^{21}$ are defined in claim 1.

11. A compound of claim 1, or a pharmaceutically acceptable salt thereof, wherein $R^3$ is aryl-substituted aryl, heteroaryl-substituted aryl, aryl-substituted heteroaryl or heteroaryl-substituted heteroaryl, aryl-substituted cycloalkyl, heteroaryl-substituted cycloalkyl, aryl-substituted alkyl, heteroaryl-substituted alkyl, aryl-substituted cycloalkyl or heteroaryl-substituted cycloalkylalkyl.

12. A compound of claim 1 wherein $R^3$ is

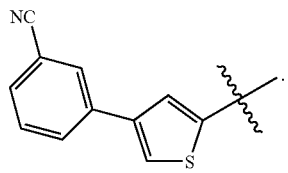

or a pharmaceutically acceptable salt thereof.

13. A compound, or a pharmaceutically acceptable salt thereof, with the following structure:

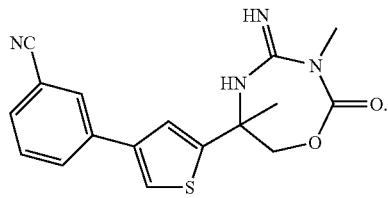

14. A pharmaceutical composition comprising at least one compound of claim 1, or a pharmaceutically acceptable salt thereof, and a pharmaceutically acceptable carrier.

15. A pharmaceutical composition comprising at least one compound of claim 13, or a pharmaceutically acceptable salt thereof, and a pharmaceutically acceptable carrier.

16. A pharmaceutical composition comprising at least one compound according to any one of claim 1 or claim 13, or a pharmaceutically acceptable salt thereof, in combination with at least one additional therapeutic agent other than a compound of claim 1 or claim 13, and a pharmaceutically acceptable carrier.

17. A pharmaceutical composition according to claim 16, wherein said at least one additional therapeutic agent is at least one agent selected from the group consisting of; a cholinesterase inhibitor, a muscarinic m1 agonist or m2 antagonist, an HMG-CoA reductase inhibitor and a non-steroidal anti-inflammatory agent.

18. A pharmaceutical composition according to claim 16, wherein said at least one additional therapeutic agent is a cholinesterase inhibitor selected from the group consisting of: donepezil, rivastigmine, galantamine, pyridostigmine and neostigmine.

19. A pharmaceutical composition according to claim 16, wherein said at least one additional therapeutic agent is an HMG-CoA reductase inhibitor selected from the group consisting of: atorvastatin, lovastatin, simvastatin, pravastatin, fluvastatin and rosuvastatin.

20. A pharmaceutical composition according to claim 16, wherein said at least one additional therapeutic agent is a non-steroidal anti-inflammatory agent selected from ibuprofen, relafen and naproxen.

* * * * *